United States Patent
Lee et al.

(10) Patent No.: US 6,652,918 B1
(45) Date of Patent: Nov. 25, 2003

(54) METHOD OF TREATING CERAMIC SURFACES

(75) Inventors: Cheng-Tsin Lee, Union City, CA (US); Keith A. Ferguson, San Mateo, CA (US); Esteban V. Herreria, Redwood City, CA (US)

(73) Assignee: The Morgan Crucible Company PLC (GB)

( * ) Notice: Subject to any disclaimer, the term of this patent is extended or adjusted under 35 U.S.C. 154(b) by 0 days.

(21) Appl. No.: 09/458,616

(22) Filed: Dec. 10, 1999

Related U.S. Application Data

(60) Provisional application No. 60/111,887, filed on Dec. 11, 1998.

(51) Int. Cl.[7] ................................................. B05D 3/00
(52) U.S. Cl. ........................ 427/387; 427/314; 427/299; 427/294; 427/255.27
(58) Field of Search ................................. 427/387, 294, 427/314, 299, 255.27

(56) References Cited

U.S. PATENT DOCUMENTS

| | | | | |
|---|---|---|---|---|
| 3,904,787 | A | * 9/1975 | Trebinger et al. | 427/220 |
| 4,015,031 | A | * 3/1977 | Reinhardt et al. | 427/213 |
| 4,387,195 | A | * 6/1983 | Tully et al. | 525/475 |
| 4,737,251 | A | 4/1988 | Carle et al. | |
| 5,158,829 | A | * 10/1992 | Wegmann et al. | 428/411.1 |
| 5,204,296 | A | * 4/1993 | Walter et al. | 501/97 |
| 5,730,598 | A | * 3/1998 | Story et al. | 433/201.1 |
| 5,798,144 | A | * 8/1998 | Varanasi et al. | 427/384 |
| 6,060,113 | A | * 5/2000 | Banno et al. | 427/78 |

FOREIGN PATENT DOCUMENTS

JP          8120225 A      5/1996

OTHER PUBLICATIONS

European Patent Office Search Report in related Application No. 99309936.5.
Aiguo, et al., "Wettability of transition metal oxide surfaces," *Materials Science & Engineering A*: Structural Materials: *Properties, Microstructure and Processing*, A242:50–56 (1998) (Abstract).
Nagai, "Planarization of Surface of Aluminium Nitride Substrate with Thin Silicon Oxide Film," *Journal of the Ceramic Society of Japan, Int. Edition*, 104–701–704 (1996).
Hiemenz, P.C., "Principles of Colloid and Surface Chemistry," *Marcel Dekker, Inc.*, pp. 209–251 (1977).
Garrett, R.H. and Grisham, C.M., "Biochemistry," 4th edition, *Saunders College Publishing, Harcourt Brace College Publishers*, pp. 46–48 (undated).
"2–D Electrophoresis Using Immobilized PH Gradients, Principles & Methods," *Amersham Pharmacia Biotech*, Rev A / 10–98, pp. Introduction and 14–18.

* cited by examiner

*Primary Examiner*—Michael Barr
(74) *Attorney, Agent, or Firm*—Dean W. Russell; Kilpatrick Stockton LLP

(57) ABSTRACT

The invention relates to methods for treating ceramic surfaces to decrease their wettability by aqueous solutions. One method involves polishing the ceramic surface until wettability is decreased, and a second method involves a silane heat treatment. Both methods can be used to produce ceramic supports for IEF and electrophoresis gels, as well as microarray plates.

27 Claims, No Drawings

METHOD OF TREATING CERAMIC SURFACES

METHOD OF TREATING CERAMIC SURFACES

This application claims benefit of the filing date of U.S. Provisional Application Ser. No. 60/111,887, filed Dec. 11, 1998, the entire contents of which is hereby incorporated by reference.

BACKGROUND OF THE INVENTION

1. Field of the Invention

The invention relates to methods for modifying the surfaces of ceramic materials in order to alter the interfacial energy of these surfaces with liquids, thereby rendering the ceramic materials more suitable for use as sample holders for electrophoresis and/or isoelectric focusing. The invention also relates to devices made with ceramics having such modified surfaces, and in particular relates to ceramic vessels used in electrophoresis.

2. Description of Related Art

The ability of a liquid phase to wet a solid phase is related to the difference between the work of adhesion (i.e., the work required to separate the immiscible liquid and solid phases) and the work of cohesion (i.e., the work required to separate the liquid from itself). If the work of adhesion is sufficiently greater than the work of cohesion, the liquid-solid system will have a positive spreading coefficient, and wetting of the solid by the liquid will spontaneously occur. If the work of cohesion of the liquid is greater than the work of adhesion, the spreading coefficient will be negative, and wetting will not spontaneously occur (because additional work will be required to overcome the attraction of the liquid for itself and make it spread across the solid surface). The determination of works of adhesion, works of cohesion, and spreading coefficient are related to the surface tension, and to the closely related concept of contact angle.

Surface tension can be thought of as the change in Gibbs free energy per unit change in the surface area. Contact angle is measured at a gas, solid, liquid interface of a sessile or pendant drop of liquid on a solid surface, typically by an optical comparator. A larger contact angle, $\theta$, indicates a decreased wetting by the liquid of the solid. A contact angle of 0 indicates that the liquid completely wets the solid. See Hiemenz, Principles of Colloid and Surface Chemistry, Marcel Dekker, 1977, pp. 209–251, the entire contents of which is hereby incorporated by reference.

Isoelectric focusing (IEF) is a technique widely used to separate proteins according to their different isoelectric points. A sample containing proteins to be separated is placed on a gel, often a single lane gel or gel strip having a pH gradient (such gels are typically obtained by electrophorescing carrier ampholytes through the gel or by covalently incorporating a gradient of acidic and basic buffering groups when the gel strip is cast). The protein molecules migrate along the gel in response to an applied electric field until they reach a point in the gel where the gel pH matches the protein's isoelectric point (i.e., the pH at which the net charge on the protein is zero). Isoelectric focusing can be used to discriminate between proteins having differences in isoelectric point as small as 0.01. See Stryer, Biochemistry, 4th. ed., pp. 46–48, the entire contents of which are hereby incorporated by reference.

In order to increase resolution of the isoelectric focusing, it is desirable that the proteins be denatured prior to and during separation. Denaturation helps to provide a single protein configuration for each protein, and to minimize interactions between protein molecules or aggregation, as well as to expose internal ionizable amino acids. Denaturation, as well as solubilization of the protein, is typically achieved by placing the protein in a solution containing urea and/or detergent prior to application to the gel.

In SDS-PAGE (sodium dodecyl sulfate-polyacrylamide gel electrophoresis), mixtures of proteins are separated according to the difference in protein molecular weights. The protein is contacted with SDS, which is an anionic detergent. The detergent both denatures the protein, and provides a large negative charge to the protein molecules, swamping the effect of any charge carrying groups on the protein itself, and providing a mechanism by which the protein will migrate in an electric field. The protein mixture is typically combined with SDS or applied to a gel containing SDS, and electrophoresed down the gel, so that proteins having lower molecular weights travel farther.

Two-dimensional (or 2-D) electrophoresis is a widely used method for the analysis of complex protein mixtures extracted from cells, tissues, or other biological samples. The technique sorts proteins by combining the IEF and SDS-PAGE techniques in two discrete steps. In one of these steps, generally the first step, IEF is used to separate the proteins according to their differing isoelectric points. The other, generally second, step separates the proteins according to their molecular weight, using SDS-PAGE gel electrophoresis. The molecular weight separation is carried out across a dimension of the gel normal to the first dimension of the gel (i.e., normal to the pH gradient). Typically, this is done by placing the strip obtained from IEF across the top of a polyacrylamide gel containing SDS and applying an electric field. The result is a two-dimensional "map" of spots of separated proteins, each having a characteristic pI and molecular weight. With a large enough gel, 2-D electrophoresis can be used to separate large numbers of different proteins from a single sample. In addition to providing information about the isoelectric points, and apparent molecular weights of these proteins, the amount of protein present in the sample may also be determined. 2D electrophoresis is also useful to analyze cell differentiation, detect disease markers, monitor therapies, micropurify proteins, as well as in cancer research and drug discovery.

The gels used for isoelectric focusing and for 2-D electrophoresis can be supplied in the form of prepared strips that are then supported by a stripholder. Solution to rehydrate the strips and/or apply the sample thereto may be supplied to the stripholder, and the strip inserted.

Ceramic materials, while desirable for use in electrophoresis equipment due to their high electrical breakdown strength, high thermal conductivity, chemical inertness, and low cost, can create problems in such applications due to the somewhat hydrophilic nature of the ceramic surfaces. In particular, when used to make stripholders of the type described above, the urea-containing and/or detergent containing protein carrying solutions tend to wick over the stripholder walls. The wicking solutions carry protein sample with them, leading to loss of sample material and potentially inaccurate results of the isoelectric focusing and 2-D electrophoresis.

Similar problems occur with ceramic materials used for microarrays of multiwell plates used in combinatorial chemistry.

Accordingly, there is a need in the art for methods of treating ceramic surfaces to lessen or avoid the wicking phenomenon responsible for sample loss and potentially inaccurate electrophoresis results, and for ceramic surfaces so treated and for articles, in particular IEF and electrophoresis sample holders, made therefrom.

SUMMARY OF THE INVENTION

The invention provides two methods for modification of ceramic surfaces so as to reduce or avoid the wicking phenomenon associated with sample loss and potential inaccuracies in IEF or electrophoresis sample holders.

In one method, the surface of the ceramic material that will come into contact with aqueous solutions is mechanically polished with an abrasive material until the wettability of the ceramic surface by the aqueous solution is decreased. This decrease is sufficient to lessen or prevent wicking. In a particular embodiment of this method, the ceramic surface is the surface of a IEF or gel electrophoresis sample holder or a microarray plate for use in combinatorial chemistry.

In another method, the surface of the ceramic material is modified by a silane heat-treatment method, whereby a silane is contacted with the ceramic surface and heated for a sufficient time and at a sufficient temperature to decrease the wettability of the ceramic surface (and, it is believed, the silane is covalently reacted with the hydroxyl moieties on the ceramic surface). In a particular embodiment of this method, the ceramic surface is the surface of a IEF or gel electrophoresis sample holder or a multiwell microarray plate for use in combinatorial chemistry. Desirably, these sample holders have a ceramic surface having a contact angle of greater than about 40° when in contact with an aqueous solution of from about 6 M to about 9.8 M urea.

Both methods are believed to modify the surface characteristics of the ceramic material in such as way as to decrease its ability to adhere to aqueous solutions, including aqueous solutions of biological molecules, such as urea-containing or detergent-containing electrophoresis solutions. This decreased adhesion (i.e., increased hydrophobicity) between the ceramic material and the aqueous solutions leads to decreased wettability, as measured by an increase in contact angle. The resulting ceramic material is suitable for use in articles requiring decreased wettability, and in particular, for gel or gel strip holders used in IEF or 2-D electrophoresis and microarrays or microwell plates of the type used in combinatorial chemistry. When used in these applications, the ceramic material prepared by the invention lessens or avoids the loss of sample material that has resulted from wicking of sample solutions out of the ceramic container. This avoidance of sample material loss increases the accuracy and reliability of the IEF, SDS-PAGE, combinatorial, or other analytical procedures carried out on the sample.

DETAILED DESCRIPTION OF SPECIFIC EMBODIMENTS OF THE INVENTION

As described above, one embodiment of the invention is directed to a method for the mechanical polishing of the ceramic surface is one method disclosed for the reduction of wetting by the solution(s). Polishing can be achieved through several standard methods; these methods include, but are not limited to: lapping, tumbling, vibratory milling. These procedures can be carried out with a slurry containing the abrasive or abrasives. Contact with a rotating polishing wheel containing the abrasive may also be used. The abrasives used may be of any form and of any particle size that will provide the desired results. Diamond particles have been found to be suitable, in particular diamond particles having a particle size ranging from about 3 microns to about 9 microns, and having an average particle size of around 6 microns. Silicon carbide particles can also be used, in particular those having a similar range of particle sizes and a similar average particle size.

Polishing is generally completed when the ceramic surface has been rendered visibly reflective. More particularly, the surface finish can be checked after polishing to determine if sufficient polishing (i.e., a sufficient polishing time) has occurred. Polishing can generally be discontinued when the surface finish ranges from about 8 to about 15 microinches (about $2 * 10^{-5}$ cm to about $4 * 10^{-5}$ cm). Typically, this will require a polishing time of about 10 sec. to about 20 sec. per square centimeter of surface.

Following polishing, the ceramic surface is cleaned to remove any remaining abrasive particles and/or abraded pieces of ceramic material. For example, the surface can be wiped, e.g., with a paper towel, contacted with a water solution of dishwashing detergent (e.g., Dawn), spray rinsed with warm tap water. This can be repeated several times as needed. A final rinse with deionized water and drying with, e.g., a paper towel can then be conducted.

The mechanical polishing process of the invention can increase the contact angle between ceramic materials, such as alumina, and solutions, such as aqueous urea solutions, from about 15° to about 20°, prior to treatment, to above about 40° after treatment.

As also described above, the wettability of ceramic surfaces can be modified by a silane heat treatment according to the invention, and this modification lessens the ability of aqueous solutions, such as protein solutions containing denaturing agents, to spread or wick over the ceramic surface. While not wishing to be bound by any theory, it is believe that this decreased wetting results at least in part because reaction of the silane with isolated hydroxyl moieties on the ceramic surface in effect removes the hydrophilic nature of these moieties with hydrophobic alkyl-containing silane groups. These isolated hydroxyl moieties can be thought of as chemically bonded water that is not easily removed from the surface of the ceramic material. Normally, they are removed only with great difficulty, requiring very high temperature exposure (e.g., exposure to temperatures of around 800° C. to around 1200° C.). Under this theory, the method for modifying a ceramic surface, comprises, (a) contacting the surface with an alkyl-containing silane; and (b) heating the surface and the alkyl-containing silane under conditions sufficient to react at least a portion of the hydroxyl groups on ceramic surface with the alkyl-containing silane.

The reaction is believed to proceed as shown in equation (1):

$$Y\text{—}OH + Si(X)_n(alkyl)_{4-n} \rightleftarrows Y\text{—}O\text{—}Si(X)_{n-1}(alkyl)_{4-n} + HX \quad (1)$$

where n is an integer between 1 and 3, Y is an inorganic species capable of binding to hydroxyl moieties at the ceramic surface, and X is halogen or other suitable leaving group. The reaction of TMCS with an alumina-containing ceramic material is provided below in equation (2) as a more specific example (it will be understood by those skilled in the art that both Y and Al are bonded to other atoms in the ceramic material, which other atoms are not shown in the interest of convenience:

$$Al\text{—}OH + Si(Cl)(CH_3)_3 \rightleftarrows Al\text{—}O\text{—}Si(CH_3)_3 + HCl. \quad (2)$$

The silane heat treatment procedure can, of course, be combined with other techniques for removing physically bonded water and for removing chemically bonded water in the form of adjacent hydroxyl moieties (both of which can be accomplished by heating, as described in more detail below).

The ceramic surface to be treated may be of any ceramic material that may come into contact with aqueous solutions under conditions where wettability must be lessened or minimized. Often, the ceramic surface will be alumina or an alumina-containing material. The aqueous solutions may be solutions of detergent and/or urea, e.g., aqueous solutions containing about 6 M to about 9.8 M urea.

The ceramic surface is contacted with the alkyl-containing silane capable of reacting with the surface hydroxyls. This silane may be a methyl-containing silane, more particularly a methyl-containing silane having a halo-silyl bond. Trialkylhalosilanes, in particular trimethylhalosilanes such as trimethylchlorosilane (TMCS), trihaloalkylsilanes, in particular trihalomethylsilanes, such as trichloromethylsilane, and dialkyldihalosilanes, in particular dimethyldihalosilanes, such as dimethyldichlorosilane are examples of suitable silanes. The silane may be applied as a solution in a solvent (e.g., ethanol) in a concentration of between about 5 wt % and about 100 wt %, or may be applied neat. The length of contacting time may vary with the ceramic material, but is long enough to sufficiently react available hydroxyl moieties and provide the requisite hydrophobicity (or at least decrease in hydrophilicity). Typical contact times range from about 1 min. to about 60 min, more particularly around 10 min. The silane used in the contacting step may be in the form of either a liquid or a vapor.

After the requisite contact time has elapsed, the coated ceramic material is heated in order to remove residual unreacted silane and to stabilize the reaction surface. Heating can be at any temperature between about room temperature and about 800° C., but typically is conducted at a temperature of about 200° C. to about 500° C., more particularly, about 200° C. to about 400° C. Heating is carried out for a period of time sufficient to remove residual unreacted silane and stabilize the surface, typically ranging from about 10 min. to about 90 min., more particularly about 30 min. The heating can be carried out in an inert environment (e.g., in an Ar or $N_2$ atmosphere, or in a vacuum), in a reducing atmosphere (e.g., in the presence of $H_2$ or CO), or in an oxidizing atmosphere (e.g., in the presence of air, $O_2$, $CO_2$, etc.). When an inert atmosphere is used, the maximum heating temperature is typically the decomposition temperature of the Si—$CH_3$ group (a temperature of approximately 800° C. will produce SiC). When an oxidizing atmosphere is used, the maximum heating temperature is typically the oxidizing temperature of the Si—O—$CH_3$ group, which is typically about 400° C.

As an example of a suitable contacting/heating arrangement, the silane heat treatment can be performed in a glove box under a nitrogen atmosphere, which reduces reaction of the silane with moisture contained in the air. The presence of organic materials, e.g., Tygon tubing in process equipment, is desirably avoided during the contacting and subsequent heating step, since most organic materials will also react with the silane, potentially reducing the effectiveness of the treatment.

The silane heat treatment of the invention is capable of increasing the contact angle between ceramic materials, such as alumina, and solutions, such as aqueous solutions of urea from about 15° to about 20°, prior to treatment, to above about 40°, more particularly above about 80° to about 90°, or even higher, after treatment.

As described above, the silane heat treatment can be combined with other methods for removing physically bonded water and more easily removable chemically bonded water, and these methods are typically performed prior to the silane heat treatment step. For example, physically bonded water (e.g., water bonded to surface hydroxyl groups or to other surface species by hydrogen bonding) can be removed by heating the ceramic material to a temperature ranging from around 70° C. to around 150° C., more particularly, around 110° C. to around 120° C., for periods of time ranging from about 10 min. to about 120 min., more particularly, about 30 min. to about 60 min. Other suitable methods for removing physically bonded water include vacuum treatment (i.e., placing the ceramic material in a pressure sufficiently below atmospheric for a sufficient time that the physically bonded water is released), and solvent washing (e.g., contacting the ceramic surface with a water miscible solvent such as acetone). Chemically bonded water tied up in adjacent surface hydroxyl groups can be removed by heating the ceramic material to a temperature of about 500° C.

Both mechanical polishing and silane heat treatment may, if desired, be carried out on the same material.

EXAMPLES

The invention is further described below with respect to nonlimiting examples thereof, which are not intended to restrict the scope of the invention in any way.

Example 1

Mechanical Surface Polishing Method

The internal walls of an alumina electrophoresis stripholder were polished using a rotating polishing wheel and a slurry containing diamond particles approximately 6 microns in average diameter, and having a particle size distribution of:

| 5%      | 10%     | 50%     | 90%     | 95%     |
|---------|---------|---------|---------|---------|
| >7.8 µm | >7.2 µm | >5.8 µm | >4.8 µm | >4.5 µm |

Prior to polishing, the surfaces were visibly dull, and an aqueous solution of urea (a typical protein carrying solution) was observed to readily wick up the sides of the strip holder. Polishing was carried out for 10–20 sec. per $cm^2$ of surface.

After polishing, the ceramic surface was cleaned by wiping off excess polishing material with a paper towel, repeatedly (6 times) dipping and shaking the material in a 20 ml/L solution of DAWN dishwashing detergent at room temperature for about 5 seconds and spray rinsing, finally rinsed with deionized water at room temperature, and wiping dry with paper towel. The surface was visibly reflective (shiny) and urea was observed to remain in the bottom of the stripholder and not wick up the polished stripholder walls. Contact angle for a urea solution of the type typically used for electrophoresis of proteins increased from 15–20° before polishing to 40–50° after polishing. Polishing of the ceramic thus increased the urea contact angle and minimized urea wetting.

Example 2

Silane Heat Treatment

An alumina electrophoresis stripholder was heat treated at 110° C. for 30 minutes to remove physically attached water.

The alumina was then dipped into a trimethylcholorosilane (TMCS) solution for 15 minutes. After the treatment, the sample was heated to a temperature (400° C.) in an oven to complete the reaction and remove the residual silane. After the treatment, the contact angle between urea and the treated alumina surface was measured using an optical comparator by OGP, Inc. Values measured after the silane treatment were 80–90°; the contact angle for non-treated samples was 15–20°. This large increase of contact angle demonstrates that the solution wetting was drastically reduced by the silane treatment. Following the treatment, tests were also done to insure the durability of the modified surface. Two cleaning tests were performed: 1.8 hours in an ultrasonic bath with 20 cc/liter Dawn detergent at 85° C.; 2.300 scrubs with a medium nylon brush (medium pressure to insure bristle ends made right angle contact with surface); In both cases, the surface appeared to be durable and functioned the same before and after the cleaning tests.

The invention having been thus described by reference to various specific embodiments, it will be apparent that other variations and modifications are possible that do not depart from the spirit of the invention, and such are intended to be encompassed within the scope of the appended claims or equivalents thereto.

What is claimed is:

1. A method for modifying an outer ceramic surface, comprising contacting the outer ceramic surface with a silane and heating for a sufficient time at a sufficient temperature to decrease the wettability of the outer surface of the ceramic by aqueous solutions, wherein the outer ceramic surface exhibits a contact angle with an aqueous solution that increases from about 15–20 degrees prior to modifying to up to about 80–90 degrees after modifying.

2. A method for modifying an outer surface of a ceramic, comprising,
   (a) contacting the outer surface of the ceramic with an alkyl-containing silane; and
   (b) heating the outer surface and the alkyl-containing silane under conditions sufficient to react at least a portion of the hydroxyl groups on the outer ceramic surface with the alkyl-containing silane, wherein the contact angle of the outer ceramic surface with an aqueous solution increases from about 15–20 degrees before being modified to up to about 80–90 degrees after being modified.

3. The method according to claim 1, wherein the silane is a methyl silane.

4. The method according to claim 1, wherein the silane is a halotrialkylsilane.

5. The method according to claim 4, wherein the halotrialkylsilane is trimethylchlorosilane.

6. The method according to claim 1, wherein the silane is a dihalodialklysilane.

7. The method according to claim 6, wherein the dihalodialklysilane is dichlorodimethylsilane.

8. The method according to claim 1, wherein the silane is a trihalomethylsilane.

9. The method according to claim 8, wherein the trihalomethylsilane is trichloromethylsilane.

10. The method according to claim 1, further comprising, removing unreacted residual silane from the outer surface of the ceramic.

11. The method according to claim 10, wherein the removal is accomplished by heating.

12. The method according to claim 1, further comprising removing at least a portion of physically attached water on the outer ceramic surface prior to contacting.

13. The method according to claim 12, wherein said physically attached water is removed by heating the surface.

14. The method according to claim 13, wherein the outer surface is heated to a temperature between about 70° C. and about 150° C.

15. The method according to claim 14, wherein the outer surface is heated to a temperature between about 110° C. and about 120° C.

16. The method according to claim 13, wherein the outer surface is heated for a time between about 10 min. and about 120 min.

17. The method according to claim 16, wherein the outer surface is heated for a time between about 30 min. and about 60 min.

18. The method according to claim 12, wherein said physically attached water is removed by subjecting the outer surface to vacuum.

19. The method according to claim 12, wherein said physically attached water is removed by washing the outer surface with a solvent.

20. The method according to claim 19, wherein the solvent is water miscible.

21. The method according to claim 20, wherein the water miscible solvent is acetone.

22. The method according to claim 1, wherein the contacting comprises exposing the outer ceramic surface to a silane that is either a neat liquid or in the form of a solution or vapor for a time ranging between about 1 min. and about 60 min.

23. The method according to claim 22, wherein the silane is in the form of a neat liquid.

24. The method according to claim 22, wherein the silane is in the form of an ethanol solution having a concentration of silane between about 5 wt % and about 100 wt %.

25. The method according to claim 1, wherein the heating comprises exposing the outer ceramic surface and silane to a temperature between about room temperature and about 800° for a time between about 10 min. and about 90 min.

26. The method according to claim 25, wherein the heating comprises exposing the outer ceramic surface and silane to a temperature between about 200° C. and about 500° C.

27. The method according to claim 25, wherein the heating comprises exposing the outer ceramic surface and silane to said temperature for a time between about 10 min. and about 30 min.

* * * * *